United States Patent [19]

Cohen et al.

[11] Patent Number: 4,876,403

[45] Date of Patent: Oct. 24, 1989

[54] PROCESS FOR THE RECOVERY OF ALCOHOLS USING A PERFLUORINATED IONOMER MEMBRANE

[75] Inventors: Abraham D. Cohen, Sarnia, Canada; William D. Diana, Belle Mead; James J. Baiel, Morris Plains, both of N.J.

[73] Assignee: Exxon Chemical Patents Inc., Linden, N.J.

[21] Appl. No.: 320,903

[22] Filed: Mar. 7, 1989

Related U.S. Application Data

[63] Continuation of Ser. No. 9,794, Feb. 2, 1987, abandoned.

[51] Int. Cl.⁴ .................. C07C 29/76; C07C 31/10; C07C 31/12
[52] U.S. Cl. .................................................. 568/913
[58] Field of Search ........................................ 568/913

[56] References Cited

U.S. PATENT DOCUMENTS

| | | | |
|---|---|---|---|
| 2,945,891 | 7/1960 | Van Heel | 568/888 |
| 3,035,060 | 5/1962 | Binning et al. | 568/913 |
| 3,062,905 | 11/1962 | Jennings et al. | 568/913 |
| 3,193,582 | 7/1965 | Adams et al. | 568/913 |
| 3,479,390 | 11/1969 | Blatz et al. | 560/265 X |
| 3,950,247 | 4/1976 | Chiang et al. | 568/913 |
| 4,065,512 | 12/1977 | Cares | 568/899 |
| 4,520,213 | 5/1985 | Victor | 568/913 |
| 4,532,347 | 7/1985 | Vaughan | 560/204 |
| 4,538,010 | 8/1985 | Diana | 568/918 |
| 4,798,674 | 1/1989 | Pasternak et al. | 568/913 |

FOREIGN PATENT DOCUMENTS

0827474 5/1981 U.S.S.R. ............................. 568/913

OTHER PUBLICATIONS

I. Cabasso et al., "The Permselectivity of Ion-Exchange Membranes for Non-Electrolyte Liquid Mixtures. I. Separation of Alcohol/Water Mixtures with Nafion$^R$ Hollow Fibers", J. Membrane Sci. 24, 101–119, 1985.

M. L. Langhorst, "A Hollow Fiber Device for Separating Water Vapor from Organic Vapors", Am. Inc. Hyg. Assoc. J., 44, 592, Mar. 1983.

I. Cabasso, "Organic Liquid Mixtures Separation by Permselective Polymer Membranes. 1. Selection and Characteristics of Dense Isotropic Membranes Employed in the Pervaporation Process", Ind. Eng. Chem. Prod. Res. Dev., 22, #2, 313 (1983).

Hsu and Gierke, J. Membrane Science, 13, 1983, 307–326.

S. C. Stinson, "Electrolytic Cell Membrane Development Surges", Chemical and Engineering News, Mar. 15, 1982.

Y. Yamabe, "Perfluorinated Ionomer Membranes", Kirk–Othmer Encyclopedia of Chemical Technology, (Supplement to 3rd Ed.), John Wiley & Sons, New York, New York (1984).

T. D. Gierke, G. E. Munn and F. C. Wilson, "Morphology of Perfluorosulfonated Membrane Product", pp. 192–216, Perfluorinated Ionomer Membranes, ed. A. Eisenberg and H. L. Yaeger, ACS Symp. Series 180, ACS, Washington, DC (1982).

S. J. Sondheimer et al., Rev. Macromol. Chem. Phys., C26 (3), 353–413 (1986).

Abstract, Par. 5, Techgram Japan, Chemtech, Oct. 1985, p. 605.

Primary Examiner—J. E. Evans
Attorney, Agent, or Firm—D. E. Furman; M. S. Goodwin

[57] ABSTRACT

According to the process of this invention, alcohols are recovered from aqueous acid solution by permeation of the alcohol through a perfluorinated ionomer membrane. An improved process for the manufacture of alcohols by acid absorption of olefins is also disclosed, the improvement residing in the use of a perfluorinated ionomer membrane to selectively permeate alcohols from the concentrated aqueous strong acid solution thereof co-produced in their synthesis from olefins.

36 Claims, 4 Drawing Sheets

PROCESS FOR THE RECOVERY OF ALCOHOLS USING A PERFLUORINATED IONOMER MEMBRANE

This is a continuation of Ser. No. 009,794, filed 2/2/87, now abandoned.

CROSS-REFERENCE TO RELATED APPLICATION

This application is related to our co-pending application entitled "Process for the Recovery of Alcohols Using An Organic Acid-Modified Polymer Membrane."

BACKGROUND OF THE INVENTION

1. FIELD OF THE INVENTION

This application relates to a new and novel process for recovering alcohols from aqueous acid streams. More particularly, the present application describes a process for the separation of alcohols from aqueous acid solution by permeation of the alcohol through a selectively permeable perfluorinated ionomer membrane.

2. DESCRIPTION OF THE PRIOR ART

The large-scale manufacture of alcohols from olefins is of considerable importance both for the alcohol produced and as a pathway in other processes. Isopropyl alcohol (IPA), for example, which is manufactured from propylene, is used as an ethanol denaturant and a solvent as well as in the production of acetone by catalytic dehydrogenation. Sec-butyl alcohol (SBA), obtained from butylenes, is used predominantly in the production of methyl-ethyl-ketone (MEK) by dehydrogenation.

The conventional method of obtaining alcohol from the corresponding olefin is by absorption of gaseous olefin (or "extraction" of liquid olefin) the term "absorption" will be understood to refer hereinafter to both processes) in an aqueous solution of strong acid, typically sulfuric acid. This process comprises two steps: sulfuric acid-catalyzed esterification of the olefin to give a stream identified as sulfuric acid extract (SAE) which comprises the mono-and di-alkyl esters of sulfuric acid corresponding to the olefin used, some alcohol, sulfuric acid, hydrocarbon by-product and unreacted olefin; and hydrolysis of the sulfated ester to give alcohol and sulfuric acid.

For example, the absorption of butene in sulfuric acid to form sec-butanol and the sec-butyl ester of sulfuric acid can be illustrated by the following equation:

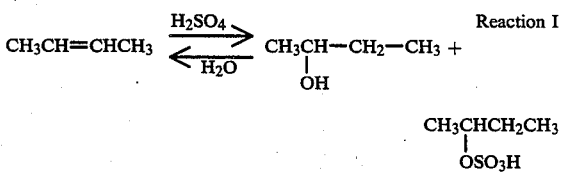

Reaction I

Thereafter, water is admixed with the SAE as it is withdrawn from the absorber in order to hydrolyze the ester and to facilitate alcohol recovery by steam stripping. There is thereby produced a diluted sulfuric acid stream which must for economic reasons be treated to concentrate it with respect to its sulfuric acid content, after which it is recycled to the olefin absorption step.

While it is also known to obtain alcohols by means of direct catalytic hydration, this process has the disadvantage of being equilibrium constrained, thus requiring olefin feeds of high purity.

Of course, other alcohols may be produced by absorption of olefins in acid, generally comprising saturated mono-alcohols having from 2 to 8 carbon atoms per molecule, and preferably having 3 or 4 carbon atoms per molecule. Examples of such alcohols are ethanol, iso-propanol, iso-butanol, sec-butanol, the pentanol isomers, etc., preferably the propanol and butanol isomers, most preferably isopropyl alcohol and sec-butyl alcohol.

Steam stripping the SBA and reconcentrating the spent sulfuric acid by distillation are both energy intensive processing steps. For example, there is an energy toll of about 1 to 2 lbs. steam/lb. alcohol product obtained in the steam stripping of the sulfuric acid extract; about 1 to 2 lbs. steam/lb. alcohol obtained, for reconcentrating the acid; and about 2 to 3 lbs. steam/lb. alcohol product obtained for, e.g., SBA distillation. Therefore, it will be apparent that means for recovering the alcohol product from the sulfuric acid stream at reduced energy cost would constitute a significant improvement over conventional practices in the manufacture of alcohols by absorption of olefins in acid.

Further, many lower molecular weight alcohols are totally miscible with and form azeotropes with water. Azeotropes at the azeotropic point give vapor of the same composition as the azeotropic liquid and thus cannot be further concentrated by normal distillation no matter how efficient the fractionating column used. Thus an alternative means to effect separation of such mixtures is highly desirable.

Various means have been suggested for improving the efficiency of such a process. U.S. Pat. No. 4,538,010, for example, describes an improved process for recovery of alcohols from the concentrated aqueous strong acid solution co-produced in their synthesis by acid absorption of olefins, the improvement residing in the use of a carboxylic acid extraction solvent to recover the alcohol from the strong acid extract, the resulting carboxylic acid extract phase being substantially free of water or strong acid. A heavy phase comprising substantially reconcentrated strong acid solution containing alkyl moieties is thereby also formed, which is suitable for recycle directly to the absorber. While the energy costs associated with acid reconcentration are thereby reduced relative to conventional processes, the large volumes of carboxylic acid extract required in the process introduce difficulties in handling as well as the added expense of the extraction solvent itself.

It is known in the art that certain membranes are permeable to molecules containing hydroxyl groups, such as water and aliphatic alcohols, and that certain of these membranes selectively permeate water over alcohols from solution containing the two. For example, U.S. Pat. Nos. 3,950,247 and 4,199,445 (the latter having issued on a divisional application based on the '247 patent), disclose a process for dehydrating aqueous solutions containing soluble organic or inorganic compounds by contacting the mixture against one side of an organic polymer membrane of polyvinyl chloride or having active anionic groups derived from strong acids, and withdrawing at the second side a mixture in the vapor phase having increased water concentration relative to the feed. Notably, in Example 1, a copolymer of styrene and acrylic acid is used to concentrate a formalin solution containing about 37% formaldehyde, 53% water, 0.05% formic acid (pKa=3.75), and 10% methanol, by selectively permeating water along with the formic acid. Thus, it is taught to use an organic polymer membrane to remove acid and water from a solution also containing alcohol and formaldehyde. In Example 7, where a sulfonated ethylene membrane was used to dewater a three-component system containing water, methanol and formaldehyde, but not acid, the order of selectivity was determined to be water>methanol>-formaldehyde. Finally, Example 18 teaches dewatering of alcohol solutions, including azeotropic mixtures, by preferential permeation of water through certain organic polymer membranes.

It is further known that certain perfluorinated ionomer membranes with pendant sulfonate groups in the hydrogen or cationated form are permeable to molecules containing hydroxyl groups, such as water and aliphatic alcohols. In Examples 14, 15 and 16 of U.S. Pat. No. 4,199,445, nitric acid solution is concentrated by permeation of water through polymer membranes containing sulfonic acid groups, including the XR membrane of DuPont, which is a sulfonated perfluorinated polymer. Cares, U.S. Pat. No. 4,065,512, teaches dehydration of t-butanol by contacting with a perfluorosulfonate acid resin while passing dry fluid on the other side of the membrane, thereby removing the water of dehydration through the membrane. Cabasso et al. describe the separation under pervaporation conditions of alcohol/water vapor mixtures by Nafion ® 811 hollow fiber membranes, the water preferentially permeating through the membrane (I. Cabasso et al., "The Permselectivity of Ion-Exchange Membranes for Non-Electrolyte Liquid Mixtures. I. Separation of Alcohol/Water Mixtures With Nafion ® Hollow Fibers," *J. Membrane Sci.* 24, 101–119, 1985). The permeability of perfluorinated ionomer membranes has also been used to advantage to separate water vapor from hydrocarbons, M. L. Langhorst, "A Hollow Fiber Device for Separating Water Vapor from Organic Vapors", *Am. Ind. Hyg. Assoc. J.*, 44, 592, March, 1983, and alcohols from hydrocarbons, I. Cabasso, "Organic Liquid Mixture Separation by Permselective Polymer Membranes. 1. Selective and Characteristics of Dense Isotropic Membranes Employed in the Pervaporation Process," *Ind. Eng. Chem. Prod. Res. Dev.*, 22, #2, 313 (1983). In Vaughan, U.S. Pat. No. 4,532,347, oxygenated hydrocarbons such as alcohols are removed from fluid mixtures by permeation through a perfluorinated membrane with an extracting solvent containing a reactant which by reacting with the hydrocarbons maintains a high concentration gradient of the hydrocarbon across the membrane.

SUMMARY OF THE INVENTION

It has been surprisingly found that alcohol can be recovered from an aqueous acid feedstream by contacting the feedstream against one side of a selectively permeable perfluorinated ionomer membrane and withdrawing at a second side of the membrane a permeate comprising alcohol in increased concentration relative to the feedstream.

This is surprising in view of the teaching in the art to employ such a membrane to permeate water from either acid or alcohol-containing solutions.

It is therefore an object of this invention to disclose a process for separating alcohol from an aqueous acid feedstream by contacting the feedstream against a selectively permeable perfluorinated ionomer membrane and by withdrawing at a second side of the membrane a permeate comprising alcohol in increased concentration relative to the feedstream.

It is another object of this invention to disclose an improved process for the recovery of alcohols from the aqueous strong acid solution co-produced in their synthesis by acid absorption of olefins.

It is a further object of this invention to obtain alcohols by acid absorption of olefins at reduced energy cost relative to conventional processes, by use of such a membrane.

It is still a further object of this invention to describe a process for producing alcohol by acid absorption of olefins wherein by use of such a membrane, acid reconcentration is accomplished without distillation.

It is an even further object to employ a membrane characterized by selectivity values with respect to the components of the aqueous strong acid solution such that alcohol and sufficient water permeate the membrane, so that there is thereby also recovered at the feed side of the membrane an acid solution which is reconcentrated with respect to acid content to a concentration suitable for direct recycle in the process.

It is an even further object to describe an energy efficient process for the manufacture and recovery of alcohols by use of such a membrane, wherein permeation of the alcohol through the membrane provides the driving force for continuous formation of the alcohol product.

DETAILED DESCRIPTION OF THE INVENTION

Prior Art Methods

Figure 1:
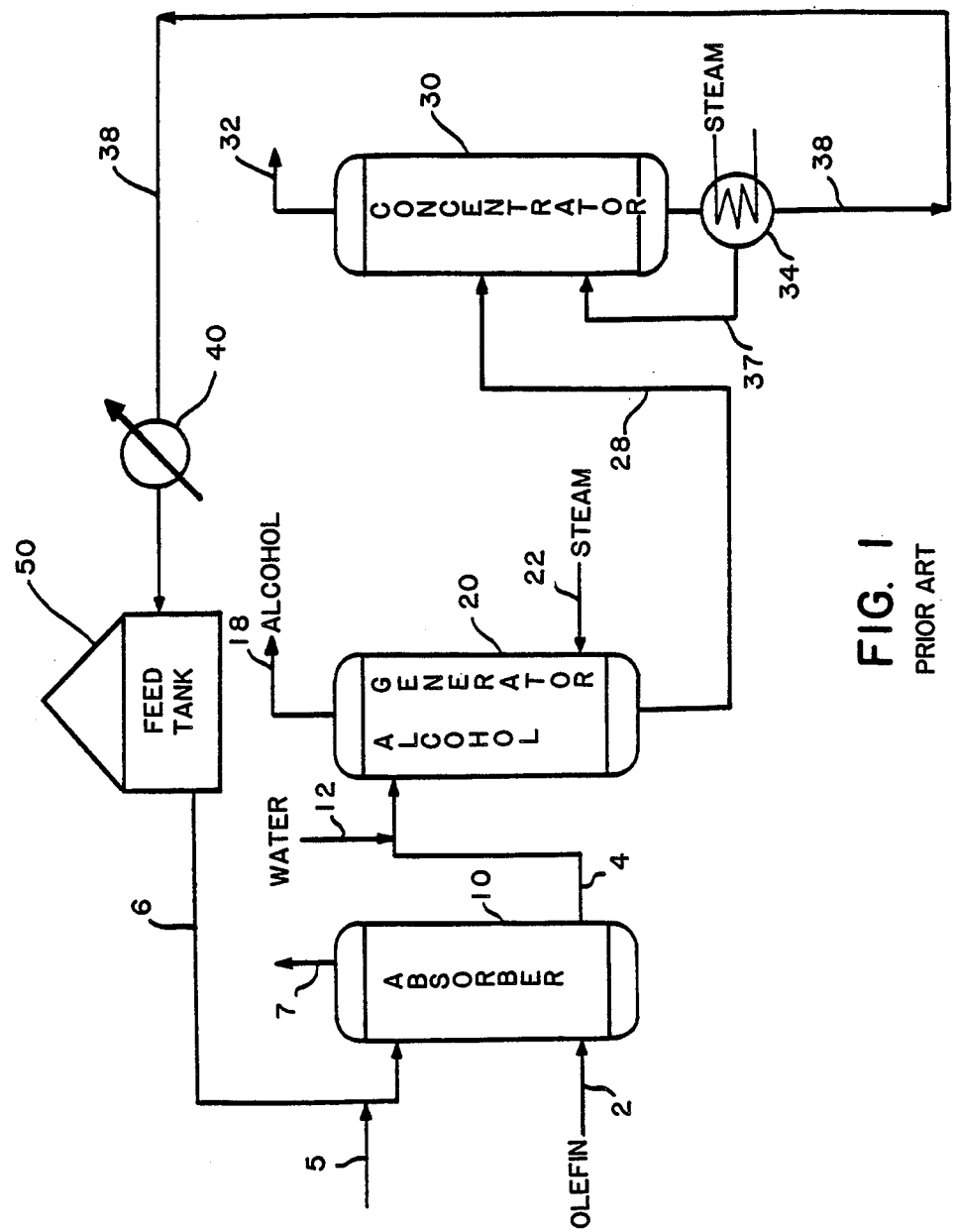
FIG. 1 is a diagrammatic illustration of a prior art process for recovery of alcohols from olefins by sulfuric acid-catalyzed hydration of the olefin, dilution of the sulfuric acid extract and steam stripping of the diluted acid extract for recovery of the alcohol vapors.

The commercial manufacture of alcohols by absorption of olefins in acid typically proceeds as illustrated in FIG. 1. Olefin feed is passed as a gas (or liquid) via line 2 to an absorber 10 wherein it is contacted with and absorbed by a concentrated aqueous strong acid stream introduced via line 6, to form the corresponding alcohol and alkyl ester of the strong acid.

The olefins to be hydrated can be obtained from any available source, such as the destructive distillation of carbonaceous materials, but particularly from the cracking of petroleum hydrocarbons such as is practiced in the petroleum refining of mineral oils. The olefin can also be conventionally obtained by careful fractionation of cracked petroleum gases and is preferably substantially free of higher unsaturates, particularly diolefins such as butadiene, etc. Illustrative of olefins which are employed are lower branched and straight-chain alkenes (i.e., alkenes of 2 to 6 carbon atoms), such as ethylene, propylene, the butylenes and the like.

The strong acid used to absorb the olefin (also termed "olefin hydration acid") generally comprises a strong organic or inorganic acid which is miscible with water and which is characterized by dissociation constants ("pK" values) in aqueous solutions of less than about 3.5. Examples of suitable inorganic olefin hydration acids are hydrofluoric acid, hydriodic acid, hydrochloric acid, ortho-phosphoric acid, phosphorous acid, perchloric acid, sulfuric acid and the like. Sulfuric acid is especially preferred. Examples of suitable organic olefin hydration acids are chloroacetic acid, benzene sulfonic acid and the like.

The aqueous concentrated acid stream 6 which is used to absorb the selected olefin feed is a concentrated acid stream whose precise acid concentration will vary depending on the olefin which is employed, the strong acid selected, the temperatures of reaction and other conditions: For example, when sulfuric acid is used as the strong acid, stream 6 will generally contain from about 45 to 85 wt. % acid strength sulfuric acid for hydration of propylene and from about 45 to 75 wt. % acid strength sulfuric acid for reaction with butylene or higher olefin feeds.

For convenience, the following discussion will be directed to the use of sulfuric acid, although it will be understood that any of the above strong acids can also be employed.

The temperature and pressure employed in absorber 10 generally also vary depending on the olefin, the acid concentration and other factors. Generally, a temperature of from about 20° to 150° C. is used, and the pressure is sufficient to maintain the desired phases in the absorber. Typically, for example, propylene is absorbed from a gas phase at a temperature of from about 90° to 150° C., and at a pressure of from about 100–500 psig.

As illustrated, the olefin and sulfuric acid streams are contacted in a counter-current fashion with the sulfuric acid stream being introduced into the upper portion of the absorber 10. Unabsorbed gases are withdrawn from the upper portion of absorber 10 via conduit 7 and can be concentrated and recycled, if desired, to conduit 2 or subjected to conventional scrubbing/washing treatment, as with caustic solutions, and vented from the process. The resulting sulfuric acid extract which is withdrawn as a liquid product via line 4 from the lower portion of absorber 10 contains water, sulfuric acid (generally in concentration of about 35 to 65 wt. %), and preferably from about 45 to 55 wt. % absorbed olefin values. The term "absorbed olefin values" is intended to refer to all molecules in the liquid which contain alkyl moieties corresponding to the olefin used, such as alkyl esters of sulfuric acid, free alcohol and free di-alkyl ether. The concentration of the alkyl ester in stream 4 can vary widely, and is generally from 15 to 30 wt. % of the total alkyl ester (mono- and di-alkyl ester) in the case of lower alkenes (e.g. propylene and butylene) absorption. For example, in the case of propylene, free isopropyl alcohol is generally present in the extract in an amount of from about 10 to 45 wt. %. The extract can also contain free di-isopropyl ether, which if present will be generally in a concentration of less than about 15 wt. %, preferably from about 3 to 6 wt. %. (Weight percent propylene values are calculated and reported herein on the basis of $C_3H_6$ moieties.) Free di-isopropyl ether, which if present will be generally in a concentration of less than about 15 wt. %, preferably from about 3 to 6 wt. %. (Weight % propylene values are calculated and reported herein on the basis of $C_3H_6$ moieties.)

Good contact between the olefin, or the mixture containing it, and the absorbing acid is important. This may be achieved, for instance, by efficient agitation or by the use of absorption towers, preferably in counter-current flow. The absorption may be continued, if desired, until the concentration of olefin in the gaseous effluent from the absorbing zone has been reduced to below about 5% by weight, and it will therefore be understood that olefin of any concentration higher than 5% in the feed can be treated.

The extent of absorption in a countercurrent system such as a series of agitator vessels and intermediates separators will depend not only on the relative amount of acid employed, but also on the length (number of stages) and capacity of the system and on the rate of throughput. Mixtures of relatively low olefin content will require a greater number of stages under otherwise similar conditions to obtain a given degree of absorption.

In the second stage of the hydration process, water is conventionally added via line 12 to the absorber product stream 4 for hydrolysis of any alkyl ester to form additional quantities of the corresponding alcohol, e.g., isopropanol from mono- or di- (isopropyl) sulfate. The manner in which the water and absorber product stream are contacted varies, and the art employs a variety of such methods, including (1) in-line addition of water (as illustrated), with a provision for a suitable length of conduit to provide adequate mixing and reaction time, and (2) contacting of the absorber product stream and water in a separate reaction vessel with agitation (not shown).

The amount of water which is added to the absorber product stream also varies widely. Generally, in conventional processes sufficient water is added in order to reduce the acid strength to from 45 to 55 wt. % acid strength sulfuric acid. These reduced acid strengths are desired to permit subsequent recovery of the alcohol by steam stripping of the alcohol-containing aqueous acidic extract.

The diluted sulfuric acid stream thus formed is generally at about 45 to 55 wt. % acid strength. The acid stream is then passed via line 4 to distillation column 20, herein termed the "alcohol generator", wherein crude alcohol is recovered as an overhead product via line 18 by steam stripping. The overhead alcohol product can then be passed to further conventional processing to produce alcohol of the required purity.

A bottoms product is withdrawn from alcohol generator 20 via line 28 and comprises a sulfuric acid stream which generally contains from about 40 to 60 wt. %, and preferably from about 45 to 55 wt. % acid strength sulfuric acid.

In conventional processes, the alcohol generator bottoms 28 are passed directly to another distillation column 30, hereinafter termed the "acid concentrator", wherein this acid stream is distilled (e.g., by use of a steam heat exchanger 34 and reboiled stream 37) for removal of water as overhead 32 and to form a second bottoms product 38 comprising a reconcentrated acid stream. These concentrated bottoms are generally cooled in cooler 40 and passed to storage tank 50 for ultimate recycle to the absorption step 10, with addition of make-up acid 5, as required.

PRESENT INVENTION

It has been found that alcohol can be recovered from an aqueous acid feedstream by contacting the feedstream against one side of a selectively permeable perfluorinated ionomer membrane and withdrawing at a second side of the membrane a permeate comprising alcohol in increased concentration relative to the feedstream.

This process may be used to advantage in the recovery of alcohols from the aqueous strong acid extract co-produced in their synthesis by acid absorption of olefins.

It is contemplated that this process may be further used to advantage in an alcohol manufacture and recovery process in combination with other membranes known to the art, to provide an alcohol recovery and acid reconcentration system which enables substantial energy savings relative to conventional processes.

Membranes effective in the present invention comprise perfluorinated ionomer membranes characterized by the presence of active anionic groups. The term "perfluorinated" refers to the replacement of hydrogen atoms in an organic compound by fluorine (except where the identity of a functional group would be altered thereby, such as in the case of per-fluoro-1-propanol). As used herein the term "perfluorinated ionomer membrane" refers to an ion-exchange membrane prepared from a perfluorinated ion-exchange polymer.

This class of ion exchange polymers is characterized by the presence of anionic groups attached to the polymer chains which are associated with protons and/or metal ions. The former exhibit acidic character while the latter show salt-like character. The anionic groups form a contiguous or nearly contiguous microphase within the polymer matrix. Examples of active anionic groups are carboxylate, sulfonate, and phosphonate.

The concentration of anionic groups can be expressed in units designated as EW (equivalent weight) which is defined as the mass in grams of the dry polymer in the acid form that would neutralize one equivalent of base. The EW of poly (acrylic acid) is 64, which is simply the molecular weight of the monomer acrylic acid. The EW of commercially available Nafion®, a perfluorinated copolymer manufactured by DuPont, usually ranges between 950 to 1,800. (See W. Y. Hsu and T. C. Giercke, "Ion Transport and Clusters in Nafion® Perfluorinate Membranes", *J. Membrane Science*, 13 [1983], 307–326.)

Polymer properties depend on the type of polymer backbone, the ionic content, the type of ionic moiety (whether carboxylate, sulfonate, or phosphonate, etc.), the degree of neutralization and the type of cation (amine, metal, hydrogen, mono-valent, multi-valent). *Kirk-Othmer Encyclopedia of Technology* (3rd Edition, Supplement Volume, pages 546–573).

A preferred membrane for use in the present process is identified in the trade as Nafion®, which is a copolymer of perfluoroethylene and perfluorovinylether, the latter component having pendant sulfonic or carboxylic acid groups. The structure of Nafion® is represented as follows, in the case of the sulfonated Nafion®:

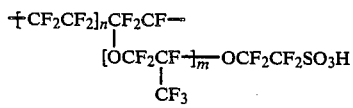

where m=5 to 13.5; n=1,000; and Z=1,2,3 . . .
Equivalent Weight (EW) Ranges 950–1,800

Cation Exchange Capacity 1.05–0.55 meq/m

Nafion® membranes are documented in the literature. (See Hsu and Gierke, *J. Membrane Science*, 13 (1983), 307–326; S. C. Stenson, "Electrolytic Cell Membrane Development Surges", *Chemical and Engineering News*, Mar. 15, 1982; Y. Yamabe, "Perfluorinated Ionomer Membranes," *Kirk-Othmer Encyclopedia of Chemical Technology* (Supplement to 3rd Ed.), John Wiley & Sons, New York, N.Y. (1984); and T. D. Gierke, G. E. Munn and F. C. Wilson, "Morphology of Perfluorosulfonated Membrane Product", pages 195–216 in *Perfluorinated Ionomer Membranes*, edited by A. Eisenberg and H. L. Yaeger, ACS Symposium Series 180 (ACS, Washington, D.C. [1982]; S. J. Sondheimer et al., Rev. Macromol. Chem. Phys., C26(3), 353–413 (1986).

Nafion® membranes can be symmetric or asymmetric. Asymmetric Nafion® membranes are comprised of material which is processed so as to produce two membrane sides having different properties such as, for example, a layer of carboxylic acid-containing resin in association with a layer of sulfonic acid-containing resin.

In practicing the separation of alcohols from acid extract the flow rate of the feed across the membrane surface should be sufficient to prevent undue selectivity loss by concentration polarization. The critical flow will depend on the particular geometry and configuration of the membrane and any supporting or containment vessel used, as well as on temperature. With higher temperatures, lower flow rates can generally be tolerated. Establishing the flow rate which is optimum for any given membrane configuration and set of operating conditions is left to the individual practitioner.

High flux can be achieved by operating with the thinnest membrane that will maintain its physical integrity under the operating conditions. To help the membrane maintain its physical integrity, a composite membrane may be used such that, e.g., a thin Nafion membrane is supported on a non-selective, highly porous membrane, thus producing a laminate wherein the selective membrane component is the Nafion component, the other porous membrane material merely constituting a physical support. The thin Nafion® membrane may range in thickness from 10 nm to 50 um.

The membrane used in the process of the present invention may be utilized in the form of hollow fibers, tubes, films, sheets, etc. The process is conveniently carried out in a diffusion cell which is divided into compartments by means of a membrane or membranes. The compartments will each have means for removing the contents therefrom. The process may be carried out continuously or batchwise, but preferably in a continuous manner.

In the process of this invention, alcohol is recovered from an aqueous acid feedstream by contacting the stream against one side of a perfluorinated ionomer membrane and by withdrawing at a second side of the membrane a permeate comprising alcohol in increased concentration relative to the feedstream.

In one embodiment, the feed is maintained under conditions of pressure such that substantially all of the alcohol is in liquid phase. The permeate is withdrawn in a vacuum, which is generally maintained in the range of 2 to 150 mm Hg. The permeated phase is generally withdrawn as a vapor and subsequently condensed. This process is known as "pervaporation".

The vacuum on the permeate side of the membrane can affect both selectivity and flux, with both selectivity and flux generally increasing as the vacuum pressure on the permeate is increased. However, the benefit of increasing the vacuum becomes insignificant at sufficiently low pressures, e.g., less than 2 mm Hg. A lower vacuum can be tolerated at higher temperatures, or with a lower boiling point alcohol (i.e., a lower vacuum can be tolerated with propanol than with butanol).

In another embodiment, a sweep gas is passed across the membrane at a rate sufficient to provide the driving force for permeation of the alcohol. Examples of suitable sweep gases are carbon dioxide, nitrogen, hydrogen, air, or low boiling hydrocarbons such as methane, ethane or propane.

Alternatively, the permeate side of the membrane may be swept by a liquid perstraction solvent in which the permeate is soluble and which is non-corrosive with respect to the membrane, at a rate sufficient to provide a driving force for permeation of the alcohol through the membrane. Examples of perstraction solvents suitable for use in the present invention include aromatic hydrocarbons such as benzene, toluene, xylene; higher molecular weight paraffins, higher molecular weight alcohols, organic acids, and compressed gases, e.g., ethane, propane, butane, etc. Especially suitable perstraction solvents are those which do not form azeotropes with the alcohol, e.g., pentane, ethylbenzene, and long chain high molecular weight alcohols.

The liquid feedstream may be contacted against one side of the membrane in any convenient manner, including continuous, semi-continuous or batchwise operations, in a single or in multiple stages.

The advantage of the present invention may be appreciated by reference to an improved process for the manufacture of alcohols by acid absorption of olefins, the improvement residing in the use of a membrane of the present invention to selectively permeate alcohols from the aqueous strong acid solution thereof co-produced in their synthesis.

Advantageously, the perfluorinated ionomer membranes of the present invention which have been found effective to separate alcohol from aqueous acid streams, are known to preferentially permeate alcohols from admixture with non-oxygenated hydrocarbons. Thus the perfluorinated ionomer membranes of the present invention are particularly useful in an alcohol manufacturing process wherein alcohol produced by acid-catalyzed hydrolysis of olefins must be separated from a reaction mixture comprising hydrocarbons, water and acid.

Figure 2:
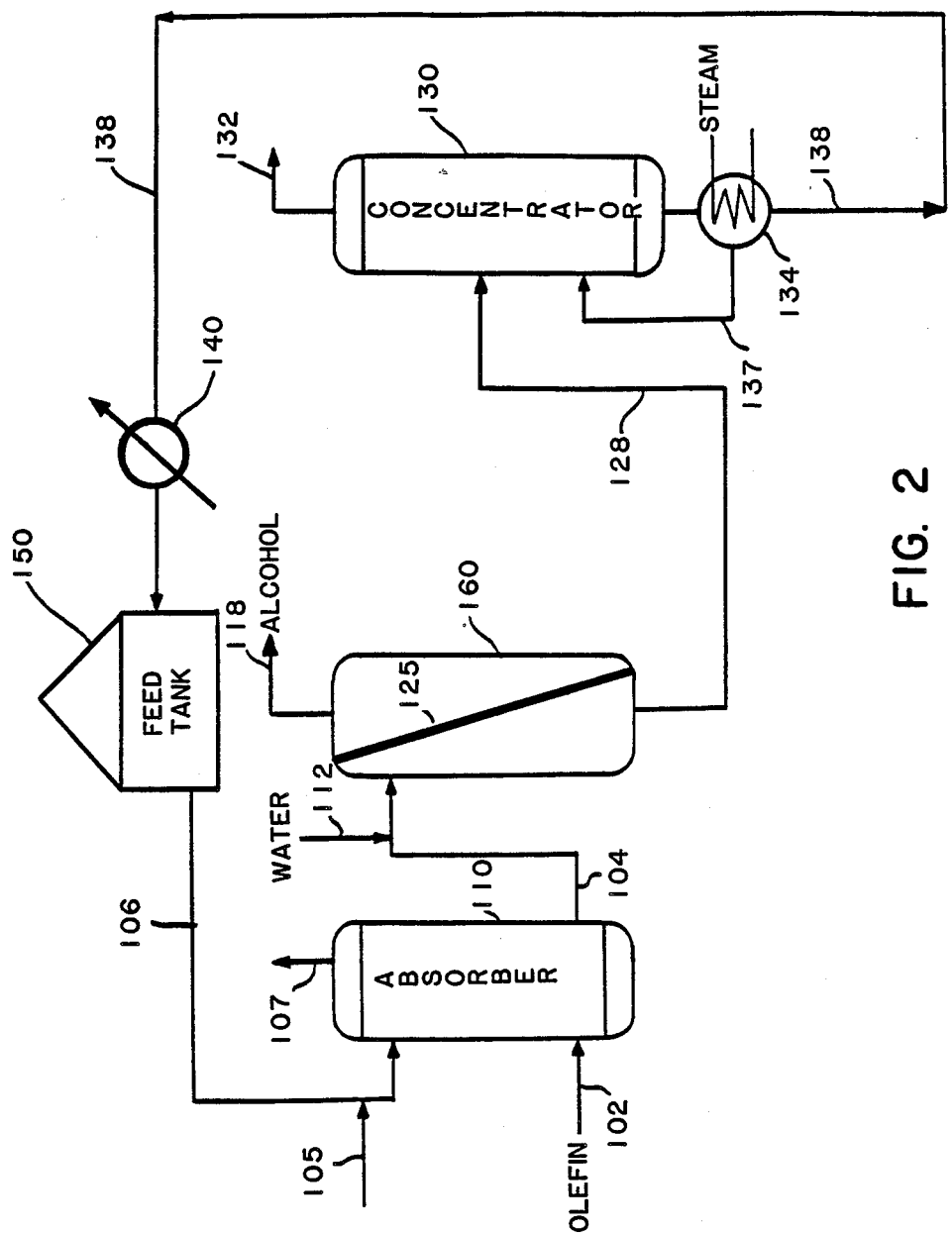
FIG. 2 is a diagrammatic illustration of one embodiment of an improved alcohol recovery process using the process of this invention.

In one embodiment of the process, as illustrated in FIG. 2, butylene feed which is passed via line 102 to absorber 110 is contacted within the absorber by a 55-85 wt. %, preferably 65 to 80 wt. %, sulfuric acid stream 106. Conditions of temperature and pressure are provided sufficient to maintain the resulting sulfuric acid extract in liquid phase, e.g., temperature in the range of 20°-150° C., preferably about 60° C., and pressure in the range of 60-500 psig, preferably about 100 psig. The extract liquid generally comprises from about 45 to 85 wt. % and more preferably from about 60 to 70 wt. % acid strength, and from about 10 to 40 wt. % absorbed butylene values, the balance being water. The extract liquid is withdrawn from the lower portion of absorber 110 via conduit 104. Unabsorbed gas, comprising butylene, is withdrawn from the upper portion of absorber 110 via conduit 107 and can be recycled if desired to conduit 102 or subjected to conventional scrubbing/washing treatment, as with caustic solutions.

Thereafter, water is added to hydrolyze the absorbed olefin values. The extract liquid is passed via line 104 to a mixing zone which can comprise a separate vessel (not shown) or a portion of the conduit 104. In the latter case, water is introduced via conduit 112 directly into conduit 104, and a suitable length of conduit should then be provided to permit the desired complete mixing and reaction of the water with the butyl sulfuric acid extract.

Alternatively, water may be added to a mixing zone in vessel 160 (not shown) wherein suitable means may be provided for adequate mixing of the water with the extract prior to contacting of the resulting diluted acid feedstream against the membrane.

The conditions under which water is added can vary widely. Generally, the temperature of the extract is maintained in the range of about 30°-100° C. The conditions of pressure under which the water is added are not critical, and pressures in the range of 50-500 psig are generally acceptable.

The diluted acid stream thus formed generally has a composition ranging from about A.S. 40-75 wt. % preferably 50-60 wt. %, and E.S. 0.2-1.4, preferably 0.8-1.2 wt. %. "A.S." refers to "acid strength", i.e., the concentration of the strong acid in the acid/alcohol feedstream, and "E.S." indicates the "Extract Saturation" of the strong acid solution.

As used herein, the "acid strength" of the acid/alcohol feedstream is defined herein on an organic-free basis as follows, in the illustrative case of $H_2SO_4$:

$$A.S. = \frac{W_1 + \frac{M_1 \times W_4}{M_1 + M_5}}{W_1 + W_2 + \frac{18W_3}{M_3} + \frac{M_1 \times W_4}{M_1 + M_5}} \times 100$$

wherein $W_1$ is the weight of strong acid, $W_2$ is the weight of $H_2O$, $W_3$ is the weight of alcohol, $W_4$ is the weight of the mono-alkyl ester of the strong acid, $M_3$ is the molecular weight of the alcohol, $M_1$ is the molecular weight of the strong acid, and $M_5$ is the molecular weight of the olefin. Also, the concentrations of the alcohol and alkyl ester in stream 104 can vary widely, and the saturated monoalcohol concentration will generally range from about 5 to 50 wt. % and preferably from about 10 to 40 wt. % and the saturated alcohol alkyl ester of the strong acid will generally range from about 1 to 15 wt. %, and preferably from about 1 to 5 wt. %, of total alkyl ester (mono- and di-alkyl ester).

As used herein, the term "extract saturation" (i.e., "E.S.") values) of strong acid solutions, containing alcohol and/or alkyl ester of the strong acid, is defined by the expression (III):

$$E.S. = \frac{^1X}{X^A}$$

wherein $X^1$ is the mole fraction of alcohol (and alcohol equivalents represented by the alkyl esters) absorbed in the liquid and $X^A$ is the mole fraction in the liquid of the strong acid and strong acid moieties of the strong acid esters.

The following feedstocks containing secondary butyl ether (SBE), butyl hydrogen sulfate (BuHSO4), sec-butyl alcohol (SBA), sulfuric acid and water are examples of those produced at higher acid concentration with water, and brought to equilibrium:

| | Feed Composition, wt. % | | | | |
|---|---|---|---|---|---|
| | SBE | BuHSO₄ | SBA | H₂SO₄ | H₂O |
| A | 0.10 | 0.05 | 6.04 | 40.48 | 53.33 |
| B | 2.88 | 0.27 | 31.36 | 31.14 | 34.34 |
| C | 0.13 | 2.12 | 6.73 | 50.37 | 40.66 |
| D | 3.46 | 10.77 | 32.65 | 30.76 | 22.36 |
| E | 0.14 | 3.19 | 6.87 | 54.09 | 35.72 |
| F | 3.67 | 15.85 | 32.49 | 29.80 | 18.18 |
| G | 0.16 | 6.31 | 6.92 | 62.46 | 24.15 |
| H | 4.13 | 29.78 | 30.79 | 25.91 | 9.39 |

The diluted sulfuric acid stream is then passed to membrane containment vessel 160 which contains therein membrane 125 of the present invention.

The specific design and configuration of the membrane containment vessel will vary according to individual requirements of capacity, flow rate, etc. The vessel should be adapted to support the membrane and to facilitate contacting of the acid stream with a first side of the membrane. Means should also be provided within the vessel for recovery of the permeate and collection of the unpermeated stream. The containment vessel should be equipped with suitable controls for maintaining desired conditions of temperature, pressure, flow rate, etc., with respect to the fluids contained therein. It is preferred that the vessel be adapted to withstand internal pressures of about 50–500 psig; temperatures of about 40°–100° C.; and flux of at least about 50–100 liters/(m² day); as well as the corrosive action of the acid feedstream.

The membrane may be formed as a flat sheet a first side of which is contacted by the acid feedstream, an alcohol-enriched permeate being recovered at a second side of the membrane. Alternatively, the membrane may comprise a hollow tube around or through which the feedstream is passed, with the permeate being collected at the inner or outer surface of the membrane, respectively.

The liquid feedstream may be contacted against one side of the membrane in any convenient manner, including continuous, semi-continuous or batchwise operations, in a single or in multiple stages.

In one embodiment of the process a vacuum is maintained at the second side of the membrane at about 0.2 psia. The diluted acid feedstream containing alcohol is contacted against one side of the membrane, and a vapor-phase permeate comprising alcohol in increased concentration relative to the feedstream is withdrawn at the second side of the membrane.

Advantageously, where the permeate is collected by pervaporation through the membrane, the heat of reaction during olefin hydration and hydrolysis of the absorbed olefin values would supply at least a part of the heat required to maintain the temperature of the permeate as it pervaporates through the membrane.

The permeate, which preferably contains at least about 60 wt. % alcohol, may then be passed via line 118 for further conventional processing, e.g., by distillation to remove excess water.

As illustrated in FIG. 2, the alcohol-depleted diluted acid stream which is thereby recovered at the feed side of the membrane, exits membrane containment vessel 160 via line 128 and is passed to acid concentrator 130 for reconcentration by distillation (e.g., using steam heat exchanger 134 and reboiled stream 137) for removal of water as overhead 132 and to form a second bottoms product 138 comprising a reconcentrated acid stream suitable for recycling in the process. The concentrated bottoms are cooled in cooler 140 and passed to storage tank 150 for ultimate recycle to the absorption step 110, with addition of make-up acid 105, as required.

The process illustrated in FIG. 2 achieves an energy savings relative to conventional processes which are characterized by the energy costly process step of steam stripping of the diluted acid feedstream to obtain an overhead alcohol-containing fraction and a diluted sulfuric acid bottoms product.

In another embodiment of the process of this invention, the membrane used is characterized by selectivity values with respect to the components of the diluted acid solution such that alcohol and sufficient water permeate through the membrane to form an aqueous permeate comprising alcohol in increased concentration relative to the feed, so that there is thereby also recovered at the feed side of the membrane an acid solution which is substantially depleted of alcohol and which is reconcentrated with respect to acid content to a concentration suitable for direct recycle in the process.

Figure 3:
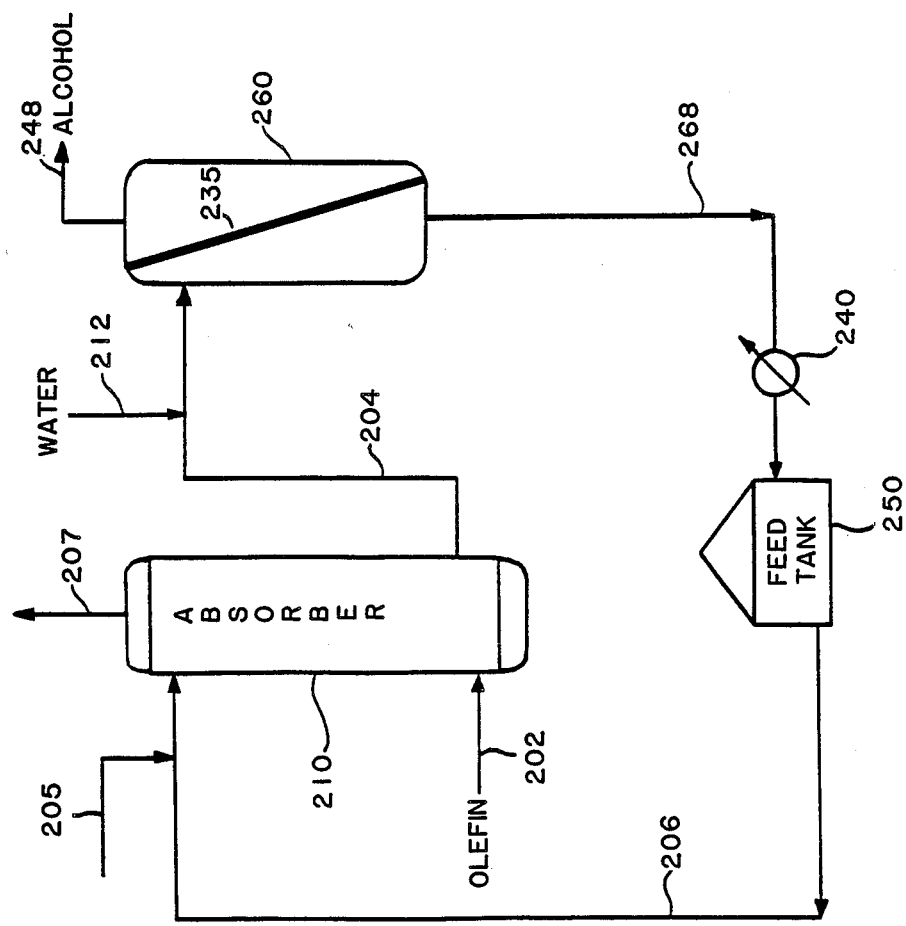
FIG. 3 is a diagrammatic illustration of a second embodiment of the process of this invention.

As illustrated in FIG. 3, butylene feed is passed via line 202 to absorber 210 for contacting within the absorber by a 55–85 wt. %, and preferably 65–80 wt. %, sulfuric acid stream from line 206. Similar conditions of temperature and pressure as in the previous embodiment are contemplated, i.e. temperature in the range of 20°–150° C. and pressure in the range of 60–500 psig. The extract liquid is withdrawn from the lower portion of absorber 210 via conduit 204. Unabsorbed gases are withdrawn from the upper portion of absorber 210 through conduit 207; and may be recycled to conduit 202 or treated conventionally by scrubbing or washing.

The liquid stream from the absorbing zone is passed via line 204 to a mixing zone (as shown, a portion of conduit 204). Water is introduced into conduit 204 via conduit 212.

The resulting diluted acid stream is then introduced into membrane containment vessel 260 and is contacted against a first side of membrane 235. According to this embodiment, an aqueous permeate containing the alcohol product permeates membrane 235 and exits the membrane containment vessel via line 248.

An aqueous concentrated strong acid solution is thereby formed of about 55 to 85 wt. %, and preferably 55 to 65 wt. % acid strength. This solution is passed via line 268 to feed tank 250 where it may be stored for eventual recycle in the process via line 206 to absorber 210, with addition of make-up acid 205, as necessary.

The alcohol-containing permeate is then passed via line 248 to a distillation tower and other conventional separations apparatus, or alternatively, is contacted against one or more membranes known in the art to be effective to separate alcohol from water solution; so as to enable recovery of the alcohol product.

The process of this invention which is illustrated in FIG. 3 achieves energy credits relative to conventional processes which require both steam stripping and acid reconcentration by distillation.

In a preferred embodiment of the present invention, a continuous low-energy process for the manufacture and recovery of alcohols is provided using a "membrane reactor unit" comprising a membrane of the present invention.

According to the process, the removal of alcohol from the liquid extract stream from the absorber, by permeation of the alcohol through the membrane of the membrane reactor unit, drives the reaction which is represented in Reaction I above, toward further absorption of the olefin in acid to form absorbed olefin values. Thus as the liquid extract stream from the absorber is contacted against a first side of the membrane, and the alcohol is removed from the extract stream by permeation through the membrane, the reaction by which olefin in the extract stream is absorbed in aqueous strong acid is driven to proceed at a rate sufficient to maintain substantially in equilibrium the liquid extract stream from the absorber with the unpermeated acid solution recovered at the first side of the membrane by permeation of the alcohol.

Since the acid-catalyzed absorption of the olefin is continuously driven by removal of the alcohol, a less concentrated aqueous strong acid may be used for absorption than was recited herein for use in the prior art processes. The aqueous concentrated strong acid used in the present process will generally comprise from about 35 to 70 wt. %, and preferably 40 to 65 wt. %, acid strength strong acid for hydration of, e.g. butylene.

In addition, since in this embodiment it is preferred that the water of hydrolysis be added to the liquid extract stream in an amount not substantially in excess of the amount sufficient to form such alcohol as will permeate the membrane, under the given conditions of flux through the membrane and to compensate for water lost by copermeation through the membrane, there is thereby avoided the acid dilution which characterizes conventional processes, and the consequent requirement for reconcentration of the acid before recycling to achieve a concentration suitable for reuse in the process.

The process achieves substantial energy savings relative to conventional alcohol manufacture and recovery processes which are characterized by the energy-intensive steps of alcohol steam-stripping and acid reconcentration. In addition, the present process improves over prior art processes which require the presence in the extract mixture of water in excess (which in prior art processes is for the purpose of diluting the acid extract to facilitate recovery of the alcohol therefrom by steam stripping). In the present process water is added stoichiometrically to form such alcohol as will permeate the membrane, and compensate for water lost by any copermeation through the membrane. Thus there is thereby avoided a shifting of the Reaction I equilibrium back to formation of the olefin and free acid which occurs in the presence of excess water.

The "membrane reactor unit" comprises one or more membranes of the present invention supported within a containment vessel which is adapted to facilitate: (1) the contacting of the liquid extract stream from the absorber with a first side of the membrane; (2) the recovery at the second side of the membrane of the permeated alcohol; and (3) the collection of the unpermeated aqueous acid solution at the first side of the membrane.

The function of the membrane reactor unit is to enable continuous removal of the equilibrium-limiting product in Reaction I above, the alcohol, so as to drive the reaction by which olefin is absorbed by aqueous strong acid toward continued formation of absorbed olefin values.

The containment vessel will preferably comprise an inlet means for introduction of the liquid extract stream containing alcohol into a first zone of the vessel; means for supporting the membrane within the vessel; a second zone of the vessel, the second zone being separated from the first zone by a membrane of the present invention; an outlet means from said second zone for recovery of the permeated alcohol; and an outlet means from said first zone for collection of the unpermeated aqueous acid solution. The vessel should be equipped with suitable controls for regulating flow rate, temperature and pressure with respect to the fluids contained therein.

Preferably the process is performed such that as alcohol is formed by hydrolysis of absorbed olefin values, the alcohol permeates the membrane, thereby facilitating recovery at the first side of the membrane of an unpermeated aqueous solution substantially in equilibrium with the liquid stream from the absorbing zone.

Figure 4:
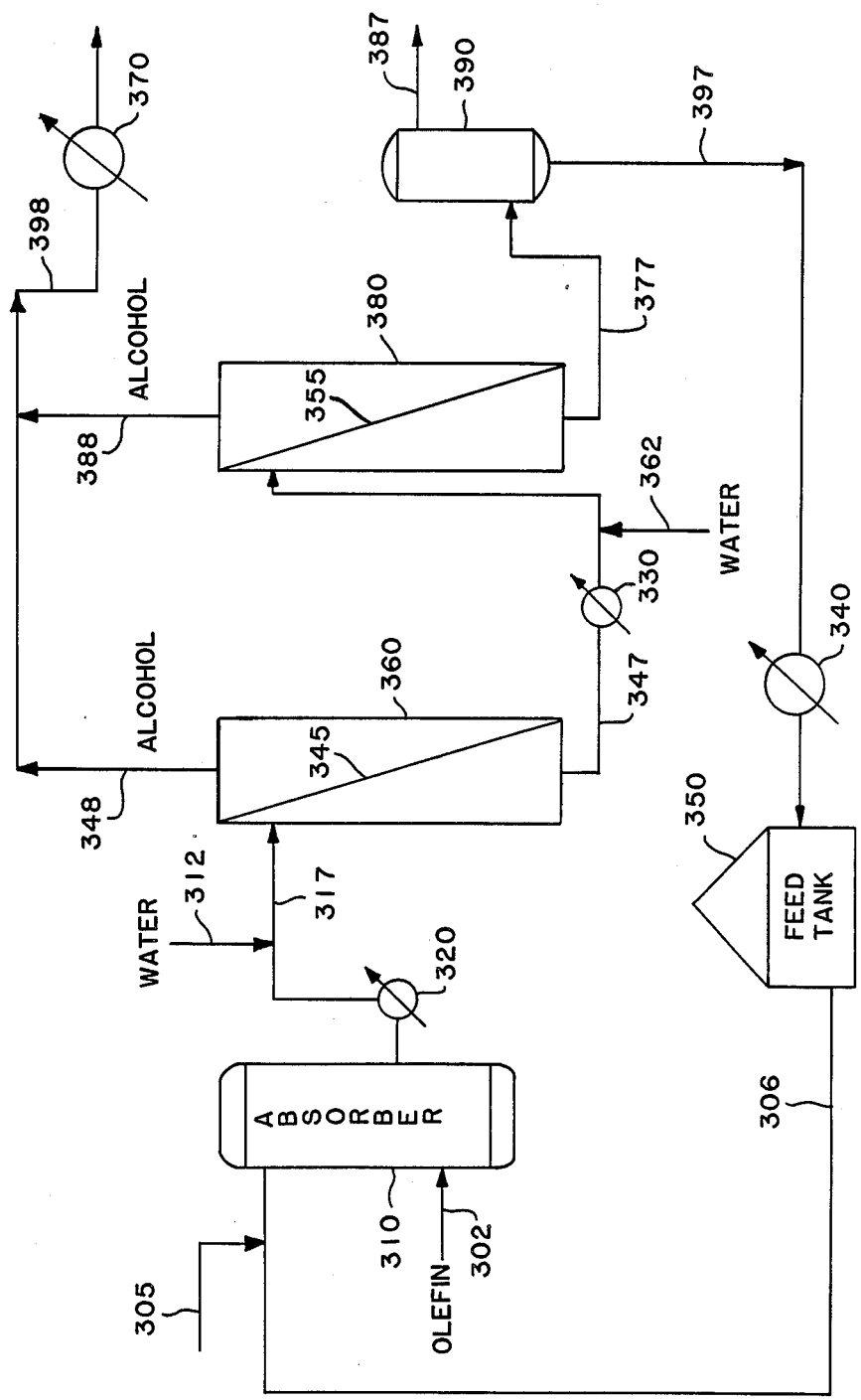
FIG. 4 is a diagrammatic illustration of a preferred embodiment of the process of this invention.

As illustrated in FIG. 4, hydrocarbon feed containing olefin such as, e.g., butylene, is introduced via line 302 into absorber 310, for contacting with aqueous concentrated strong acid, such as sulfuric acid from line 306. When sulfuric acid is used as the strong acid, stream 306 will generally contain from about 35 to 70 wt. %, and preferably 40 to 65 wt. %, acid strength sulfuric acid for hydration of the butylene. There may be present in the feed, in addition to the olefin, inert paraffins derived from the cracking of petroleum hydrocarbons to form olefins. It is preferred that the olefin comprise at least about 30 wt. % of the feed. Mixers (not shown) may optionally be used in the absorber to insure that the acid and hydrocarbon are well mixed and preferably at least partially emulsified.

The temperature and pressure employed in absorber 310 generally range from about 20° C. to 150° C. and about 100 to 500 psig, respectively. Preferably, the pressure within the absorber is sufficient to maintain the hydrocarbon feed in liquid phase.

The resulting liquid stream which is withdrawn as a liquid product via line 317 from absorber 310 contains water (preferably, about 20 to 30 wt. %), sulfuric acid (preferably, in concentration of about 60 wt. % acid strength), and about 20 to 30 wt. % absorbed olefin values and unreacted hydrocarbons, such as paraffins and tars. Thus the acid stream thus formed would have a composition of about A.S. 60 wt. % and E.S. 0.8. The liquid stream is then passed via line 317 to membrane reactor unit 360 comprising membrane 345 of the present invention.

Prior to contacting with the membrane, the liquid stream from the absorber comprising sulfuric acid extract and unreacted hydrocarbons is admixed with water to hydrolyze at least a portion of the absorbed olefin values. The water may be added by in-line addition via line 312 (as shown) to the liquid stream prior to introduction of the stream into the membrane reactor unit or alternatively by introduction into a zone within the membrane reactor unit or within a separate vessel (not shown).

It is preferred that water be added as required in an amount not substantially in excess of the amount sufficient to: (1) form such alcohol as will permeate the membrane under the given conditions of flux; and (2) compensate for any water lost by co-permeation with the alcohol through the membrane, in order that the composition of the liquid stream from the absorbing zone and the unpermeated aqueous acid solution recovered at the first side of the membrane by permeation of the alcohol are maintained substantially in equilibrium.

Advantageously, where the alcohol permeate is collected by pervaporation through the membrane, the heat of reaction during olefin hydration would supply at least a part of the heat required to maintain the temperature of the permeate as it pervaporates through the membrane. Heat exchanger 320 is provided to add or remove heat from the liquid before it contacts the membrane. Optionally, or in the alternative, a heat exchanger may be provided in line 317 after addition of water to the liquid stream.

Various configurations of the membrane and the membrane reactor unit are possible, depending on desired conditions of temperature, flux, pressure, etc. The use of a hollow fiber membrane is preferred since de-emulsification of the liquid stream during passage through the hollow fibers would be more difficult than through either plate-and-frame or spiral wound modules.

In FIG. 4, the alcohol is recovered as an overhead product via line 348 by vapor phase pervaporation through membrane 345. The overhead alcohol product can then be passed via line 398 for condensation to heat exchanger 310 and for further conventional processing, for example, to remove water copermeated with the alcohol.

The unpermeated aqueous acid solution is withdrawn from membrane reactor unit 360 through line 347.

In FIG. 4, the aqueous acid solution in line 347 comprising absorbed butylene values as well as unreacted hydrocarbons is passed to a second membrane reactor unit 380 containing membrane 355 of the present invention. Optionally, mixers (not shown) may be used to insure that the solution remains emulsified. Heat exchanger 330 is provided to add or remove heat from the liquid before it contacts membrane 355. As before, where the alcohol is to be pervaporated through the membrane the heat of reaction of the continuing hydration of the olefin would supply at least part of the heat needed to maintain the temperature of the permeate as it pervaporates through the membrane.

Water is added via line 362 to hydrolyze absorbed olefin values.

The alcohol permeate is recovered from membrane reactor unit 380 as an overhead product through line 388. The alcohol is then passed to line 398 for cooling using heat exchanger 370, and further conventional processing.

The effluent from membrane reactor unit 380 which is withdrawn through line 377 contains predominantly two phases: a spent hydrocarbon phase comprising, e.g., butanes, butadienes, and tars and oils formed by polymerization reactions; and a sulfuric acid extract phase comprising sulfuric acid and residual absorbed olefin values including alcohol. The effluent is passed to phase separator 390 for conventional separation of the two phases and removal via line 387 of the spent hydrocarbon phase. A bottoms portion comprising the sulfuric acid phase is passed via line 397 for recycling in the process. Generally this phase comprises about 7 to 17 wt. % alcohol and about 40 to 65 wt. % sulfuric acid. Heat exchanger 340 is provided to add or remove heat from the acid extract before it is passed to feed tank 350 for recycling in the process.

The acid extract, not having been substantially diluted in the process, is suitable for reuse directly to the absorber. Make-up sulfuric acid may be provided to the absorber via line 305.

It will be obvious that various changes and modifications may be made without departing from the invention and it is intended, therefore, that all matter contained in the foregoing description shall be interpreted as illustrative only and not limitative of the invention.

EXAMPLE 1

A sample approximately 5.5 cm in diameter was prepared of a perfluorinated ionomer membrane containing sulfonic groups (Nafion ® N324, DuPont), the membrane comprising a reinforced two-film composite with one layer having a thickness of about 25 $\mu$m (1 mil.) and an $SO_3H$ equivalent weight of 1,500 and another layer having a thickness of about 125 $\mu$m (5 mil.) and an $SO_3$ equivalent weight of 1,100. The membrane was mounted in a test cell of a laboratory pervaporation unit. A liquid feed comprising 16.5 wt. % SBA, 43.8 wt. % $H_2SO_4$ and 39.7 wt. % water was pumped at atmospheric pressure over the surface of the membrane at a rate of about 3 liters per minute. The permeate was withdrawn under vacuum of about 150 kPa. The vapor-phase permeate was condensed on a glass cold trap cooled by liquid nitrogen. The condensate was warmed to room temperature, and the amount of water in the condensate was determined by a Karl Fischer titration. During a test of the membrane, the permeate was sampled and analyzed for water content at hourly intervals.

The permeate comprised about 35 wt. % water and 65 wt. % organics. By gas chromatography, the organic material in the permeate was shown to be greater than about 95 wt. % SBA, with most of the remainder being dibutyl ether.

pH measurements confirmed that sulfuric acid was not present in measurable quantity either in the permeate sample or on the permeate side of the membrane surface.

A comparative test was conducted in which the feed comprised water and SBA (29.4 wt. % SBA, 70.6 wt. % $H_2O$), no sulfuric acid being present. The permeate of such a system contained about 80 wt. % water. From this it was unexpected that from a feed containing SBA, water and sulfuric acid, the alcohol would preferentially permeate a Nafion ® membrane.

EXAMPLES 2-9

Further separations were performed on various NAFION ® membranes using a 10 wt. % SBA/90 wt. % $H_2O$ solution, or on an acid extract feed consisting of 16.5/48.8/34.7% by weight SBA/$H_2SO_4$/$H_2O$ (identified as "Standard Feed") in the following Examples 2-9. The temperature was either 25° C. for water/SBA or 50° C. for Standard Feed unless otherwise indicated in the Examples.

In Examples 2 through 8 the feeds may have been contaminated with variable trace amounts of ions from the 316 stainless steel due to sulfuric acid penetrating imperfections in the Teflon coatings on the stainless steel components.

EXAMPLE 2

Nafion ®—152E 6-1124

(50 $\mu$m Thick, 1,500 $SO_3H$ Equivalent Weight)

| Sample No. | Elapsed Time, Hrs | Feed % $H_2O$ | Permeate Flux, kg/(m²d) | SBA wt. % |
|---|---|---|---|---|
| 1 | 1 | Standard | 9.0 | 28.0 |
| 2 | 2 | | 5.5 | 62.0 |
| 3 | 3 | | 6.8 | 52.0 |
| 4 | 4 | | 6.3 | 55.0 |

-continued

| Sample No. | Elapsed Time, Hrs | Feed % H₂O | Permeate Flux, kg/(m²d) | SBA wt. % |
|---|---|---|---|---|
| 5 | 5 | | 5.0 | 59.0 |
| 6 | 6 | | 4.0 | 61.0 |

The values for wt. % SBA in the permeate show good selectivity of the membrane for the alcohol relative to the other components of the acid feed.

EXAMPLE 3

Effect of Temperature

Nafion ®—Dupont Code 152E 6-1124 50 μm Thick, 1,500 SO₃H Equivalent Weight)

| Sample No. | Elapsed Time, Hrs | Temperature (°C.) | Feed | Permeate Flux, kg/(m²d) | SBA wt. % |
|---|---|---|---|---|---|
| | | Cell A | | | |
| 1 | 1 | 25 | 10% SBA | 30.8 | 26.4 |
| 2 | 2 | | | 26.3 | 18.0 |
| 3 | 3 | | | 23.8 | 16.0 |
| 4 | 1 | 28 | Standard | 1.0 | 37.0 |
| 5 | 2 | 41 | | 3.8 | 58.4 |
| 6 | 3 | | | 6.8 | 63.2 |
| 7 | 4 | 50 | | 11.3 | 67.2 |
| 1 | 1* | 40 | | 10.3 | 62.0 |
| 2 | 2 | | | 8.3 | 64.0 |
| 3 | 1 | 60 | | 15.3 | 65.3 |
| 4 | 2 | | | 14.5 | 64.2 |
| 5 | 3 | | | 15.5 | 65.7 |
| 6 | 1 | 70 | | 19.8 | 65.3 |
| 7 | 2 | | | 17.8 | 63.7 |

*The membrane was left in the unit cell exposed to the standard feed overnight. Increasing the temperature of the Standard Feed from 28° C. to 70° C. caused flux to increase while selectivity remained stable.

EXAMPLE 4

Effect of Increase in SBA Concentration

Nafion ® Dupont Code 152 ©E 6-1124 50 μm Thick 1,500 SO₃H Equivalent Weight*

| Sample No. | Elapsed Time, Hrs | Feed | Permeate Flux, kg/(m²d) | SBA wt. % |
|---|---|---|---|---|
| 1 | 1 | See Above | 7.3 | 36.4 |
| 2 | 2 | | 5.0 | 55.7 |
| 3 | 3 | | 4.8 | 55.6 |

The membrane sample used in the prior Example was used. Flux declined compared to the previous Example, probably as a result of the increase in acid concentration relative to the Standard Feed; but the membrane retained good selectivity for the alcohol.

EXAMPLE 5

Nafion ®—Dupont Code N324

(Reinforced Two Film Composite: 25 μm, 1,500 SO₃H Equivalent Weight; and 125 μm, 1,100 SO₃H Equivalent Weight)

| Sample No. | Elapsed Time, Hrs | Feed | Permeate Flux, kg/(m²d) | SBA wt. % |
|---|---|---|---|---|
| 1 | 1 | 10% SBA | 21.8 | 17.4 |
| 2 | 2 | | 21.3 | 18.5 |
| 3 | 1 | Standard | 10.5 | 46.5 |
| 4 | 2 | | 6.5 | 62.6 |
| 5 | 3 | | 5.8 | 62.5 |
| 6 | 4 | | 5.8 | 63.8 |

EXAMPLE 6

Nafion ®—Dupont Code 152E-6-1114 100 μm Thick, 1,100 SO₃H Equivalent Weight

| Sample No. | Elapsed Time, Hrs | Feed | Permeate Flux, kg/(m²d) | SBA wt. % |
|---|---|---|---|---|
| 1 | 1 | 10% SBA | 25.8 | 15.3 |
| 2 | 2 | | 23.0 | 14.0 |
| 3 | 3 | | 14.5 | 13.5 |
| 1 | 1 | Standard | 9.3 | 64.0 |
| 2 | 2 | | 8.2 | 60.1 |
| 3 | 3 | | 8.0 | 63.7 |
| 4 | 4 | | 7.5 | 62.5 |

EXAMPLE 7

Nafion ® Dupont Code 152E-6-1114—100 μm Thick, 1,100 SO₃H Equivalent Weight Membrane Details—Heat Treated Membrane*

| Sample No. | Elapsed Time, Hrs | Feed | Permeate Flux, kg/(m²d) | SBA wt. % |
|---|---|---|---|---|
| 1 | 1 | 10% SBA | 18.8 | 16.4 |
| 2 | 2 | | 20.0 | 15.8 |
| 1 | 1 | Standard | 9.4 | 62.9 |
| 2 | 2 | | 8.7 | 64.9 |
| 3 | 3 | | 7.8 | 64.8 |
| 4 | 4 | | 8.0 | 64.9 |

*The membrane was heated in air at 250° C. for two hours. The heat treated membrane showed slightly lower flux and marginally higher selectivity than the untreated membrane used in Example 6, but the differences appear to be within experimental error.

EXAMPLE 8

Nafion ®—Dupont Code E39489-1A—22 μm Thick

| Sample No. | Elapsed Time, Hrs:Mins | Feed | Permeate Flux, kg/(m²d) | SBA wt. % |
|---|---|---|---|---|
| 1 | 0.28 | 10% SBA | 340.0 | 19.7 |
| 2 | 0.57 | | 357.0 | 20.5 |
| 3 | 1.21 | | 335.0 | 20.9 |
| 4 | 0.30 | Standard | 28.5 | 77.0 |
| 5 | 1.00 | | 31.0 | 67.9 |
| 6 | 0.03 | | 54.5 | 67.2 |
| 7 | 1.00 | | 57.5 | 67.1 |
| 8 | 1.30 | | 56.3 | 67.3 |
| 9 | 2.10 | | 48.8 | 66.5 |
| 10 | 2.40 | | 71.0 | 66.3 |
| 11 | 3.10 | | 59.0 | 67.4 |
| 12 | 3.40 | | 61.5 | 67.9 |
| 13 | 4.10 | | 63.0 | 68.4 |
| 14 | 4.34 | | 67.4 | 67.7 |
| 15 | 5.04 | | 59.0 | 67.7 |

*High flux with low selectivity was observed when the SBA/water feed was contacted against the membrane. Flux dropped when the acid feed was contacted against the membrane, but high selectivity toward the alcohol was demonstrated.

EXAMPLE 9

Membrane Nafion ® 115-84-1012—125 μm, (1,100 SO₃H Equivalent Weight*)

| Sample No. | Elapsed Time, Hrs | Feed | Permeate Flux, kg/(m²d) | SBA wt. % |
|---|---|---|---|---|
| 1 | 1 | 10% SBA | 54.0 | 22.6 |
| 2 | 2 | Standard | 7.0 | 54.3 |
| 3 | 3 | | 7.3 | 69.3 |
| 4 | 4 | | 12.3 | 69.2 |
| 5 | 5 | | 10.8 | 69.1 |
| 6 | 6 | | 16.8 | 65.4 |
| 7 | 7 | | 20.5 | 61.6 |
| 8 | 8 | | 19.8 | 63.7 |
| 9 | 9 | | 19.0 | 25.8 |
| 10 | 10 | | 18.5 | 23.6 |
| 11 | 1 | 10% SBA | 68.8 | 67.1 |
| 12 | 2 | | 80.5 | 76.4 |
| 13 | 1 | Standard | 28.5 | 67.1 |
| 14 | 2 | | 27.0 | 58.9 |
| 15 | 3 | | 35.8 | 64.5 |

*Tests were run on a modified unit free of any ionic contamination possibly caused by the action of sulphuric acid on stainless steel surfaces within the unit. The stainless steel membrane support plate on the unit was replaced by a 40 mm diameter sintered glass disc. Thus, no liquid within the unit was contacted by a metal surface.

EXAMPLE 10—IPA FEED

Nafion ® —Dupont Code E39849-1A—22 μm Thick

| Sample No. | Elapsed Time, Hrs:Mins | Feed | Permeate Flux, kg/(m²d) | IPA wt. % |
|---|---|---|---|---|
| 1 | 0:30 | 10% IPA | 191.5 | 19.7 |
| 2 | 1:00 | | 190.5 | 21.2 |
| 3 | 1:30 | | 209.0 | 23.0 |
| 4 | 2:00 | | 259.0 | 21.1 |
| 5 | 1:00 | REF. 10 | 45.0 | 59.8 |
| 6 | 2:00 | | 49.0 | 62.1 |
| 7 | 3:45 | | 48.0 | 62.0 |
| 8 | 4:45 | | 63.3 | 68.3 |
| 9 | 5:45 | | 46.8 | 60.9 |

The Nafion membrane was mounted in the cell and a feed of 10% isopropyl alcohol in water was circulated at 24° C. An acid feed comprising about 27 wt. % isopropyl alcohol, 45 wt. % H₂SO₄ and 27 wt. % H₂O (herein designated "REF 10") was then circulated at 50° C. High flux with very low selectivity was observed when the IPA/water feed was contacted against the membrane. Flux decreased when the acid feed was contacted against the membrane but good selectivity toward the alcohol was observed.

What is claimed is:

1. Process for the separation of alcohol from a feed mixture comprising alcohol, water and acid, which process comprises contacting the mixture against a first side of a perfluorinated ionomer membrane and withdrawing at a second side of the membrane a permeate comprising alcohol in increased concentration relative to the feed, wherein an aqueous acid solution is recovered to the first side of the membrane, said solution being substantially depleted of alcohol.

2. Process of claim 1 wherein the aqueous acid solution contains from about 45 to 85 wt. % acid strength acid.

3. The process of claim 1 wherein the alcohol comprises a saturated mono-alcohol having from 2 to 8 carbon atoms per molecule.

4. The process of claim 1 wherein the alcohol recovered is sec-butyl alcohol and the feed from which the alcohol is recovered comprises sec-butyl alcohol, sulfuric acid and water.

5. The process of claim 1 wherein the alcohol is isopropyl alcohol and the feed from which the alcohol is recovered comprises isopropyl alcohol, sulfuric acid and water.

6. The process of claim 1 wherein the membrane comprises a copolymer of perfluoroethylene and perfluorovinylether, wherein the perfluorovinylether moiety bears pendant carboxylic acid or sulfonic acid groups.

7. The process of claim 1 wherein the membrane comprises a copolymer of perfluoroethylene and perfluorovinylether wherein the perfluorovinylether moiety bears pendant sulfonic acid groups.

8. The process of claim 7 wherein the alcohol recovered is sec-butyl alcohol and the feed from which the alcohol is recovered comprises sec-butyl alcohol, sulfuric acid and water.

9. The process of claim 7 wherein the alcohol recovered is isopropyl alcohol and the feed from which the alcohol is recovered comprises isopropyl alcohol, sulfuric acid and water.

10. The process of claim 1 wherein the membrane comprises the following copolymer:

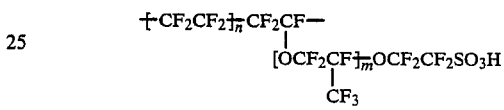

where m=5 to 13.5; n=1,000; and Z=1, 2, 3 . . .

11. The process of claim 1 wherein the permeate is withdrawn at a pressure which is less than the pressure which is maintained on the feed.

12. The process of claim 11 wherein the permeate is withdrawn at a partial pressure which is less than atmospheric pressure.

13. The process of claim 12 wherein the permeate is withdrawn as a vapor.

14. The process of claim 1 wherein a gas is passed against the second side of the membrane, the permeate vaporizing into said gas.

15. The process of claim 1 wherein a liquid solvent is passed against the second side of the membrane, the permeate being soluble in said solvent.

16. An improved process for preparing alcohols which comprises:
    (a) absorbing an olefin in an absorbing zone with an aqueous concentrated strong acid stream to form an alkyl ester of the acid corresponding to said olefin;
    (b) recovering a liquid stream from said absorbing zone containing said acid alkyl ester;
    (c) contacting said recovered liquid with water for liberation of the corresponding alcohol;
    (d) contacting the resulting diluted acid feedstream containing alcohol against a first side of a perfluorinated ionomer membrane; and
    (e) withdrawing at a second side of the membrane a permeate comprising alcohol in increased concentration relative to the feedstream, thereby also recovering at the first side of the membrane a diluted acid solution, said diluted acid solution being substantially depleted of alcohol.

17. The process of claim 16 wherein the diluted acid solution is passed to an acid concentrator wherein said acid solution is distilled for removal of aqueous vapors to form an aqueous concentrated strong acid stream containing from about 45 to 85 wt. % acid strength acid.

18. The process of claim 16 wherein the alcohol comprises a saturated mono-alcohol having from 2 to 8 carbon atoms per molecule.

19. The process of claim 19 wherein the membrane comprises a copolymer of perfluoroethylene and perfluorovinylether wherein the perfluorovinylether moiety bears pendant sulfonic acid groups.

20. The process of claim 19 wherein the alcohol is selected from sec-butyl alcohol or isopropyl alcohol.

21. The process of claim 16 wherein the permeate is withdrawn at a pressure which is less than the pressure which is maintained on the feed.

22. The process of claim 21 wherein the permeate is withdrawn at a partial pressure which is less than atmospheric pressure.

23. The process of claim 22 wherein the permeate is withdrawn as a vapor.

24. An improved process for preparing alcohols which comprises:
 (a) absorbing an olefin in an absorbing zone with an aqueous concentrated strong acid stream to form an alkyl ester of the acid corresponding to said olefin;
 (b) recovering a liquid stream from said absorbing zone containing said acid alkyl ester;
 (c) contacting said recovered liquid with water for liberation of the corresponding alcohol;
 (d) contacting the resulting diluted acid feedstream containing alcohol against a first side of a perfluorinated ionomer membrane; and
 (e) withdrawing at a second side of the membrane an aqueous permeate comprising alcohol in increased concentration relative to the feedstream, thereby also recovering at the first side of the membrane an aqueous concentrated strong acid solution containing from about 45 to 85 wt. % acid strength acid, said solution being substantially depleted of alcohol.

25. The process of claim 24 wherein the aqueous concentrated strong acid solution is recycled to the absorbing zone.

26. The process of claim 24 wherein the alcohol comprises a saturated mono-alcohol having from 2 to 8 carbon atoms per molecule.

27. The process of claim 24 wherein the membrane comprises a copolymer of perfluoroethylene and perfluorovinylether wherein the perfluorovinylether moiety bears pendant carboxylic acid or sulfonic groups.

28. The process of claim 24 wherein the membrane comprises a copolymer of perfluoroethylene and perfluorovinylether wherein the perfluorovinylether moiety bears pendant sulfonic acid groups.

29. The process of claim 28 wherein the alcohol from sec-butyl alcohol or isopropyl alcohol.

30. The process of claim 24 wherein the membrane comprises the following copolymer:

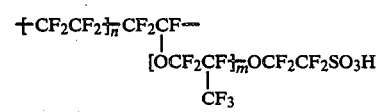

where $m = 5$ to $13.5$; $n = 1,000$; and $Z = 1, 2, 3 \ldots$

31. An improved process for preparing alcohols which comprises:
 (a) absorbing an olefin in an absorbing zone with an aqueous concentrated strong acid stream to form an alkyl ester of the acid corresponding to said olefin;
 (b) recovering a liquid stream from said absorbing zone containing said acid alkyl ester;
 (c) contacting said recovered liquid with water for liberation of at least a portion of the corresponding alcohol;
 (d) contacting the resulting acid feedstream containing alcohol against a first side of a perfluorinated ionomer membrane; and
 (e) withdrawing at a second side of the membrane a permeate comprising alcohol in increased concentration relative to the feedstream, thereby also recovering at the first side of the membrane an aqueous acid solution, said aqueous acid solution being substantially in equilibrium with the liquid feedstream from said absorbing zone.

32. The process of claim 31 wherein the aqueous acid solution is recycled to said absorbing zone.

33. The process of claim 31 wherein the alcohol comprises a saturated mono-alcohol having from 2 to 8 carbon atoms per molecule.

34. The process of claim 31 wherein the membrane compares a copolymer of perfluoroethylene and perfluorovinylether wherein the perfluorovinylether moiety bears pendant sulfonic acid groups.

35. The process of claim 34 wherein the alcohol is selected from isopropyl alcohol or sec-butyl alcohol.

36. The process of claim 34 wherein the aqueous acid solution of step (e) contains from about 40 to 65 wt. % acid strength acid.

* * * * *